US012653986B2

(12) United States Patent (10) Patent No.: US 12,653,986 B2
Ruebben (45) Date of Patent: Jun. 16, 2026

(54) KINK-PROOF BALLOON CATHETER

(71) Applicant: Alexander Ruebben, Monaco (MC)

(72) Inventor: Alexander Ruebben, Monaco (MC)

( * ) Notice: Subject to any disclaimer, the term of this patent is extended or adjusted under 35 U.S.C. 154(b) by 1089 days.

(21) Appl. No.: 17/762,737

(22) PCT Filed: Sep. 1, 2020

(86) PCT No.: PCT/EP2020/074287
§ 371 (c)(1),
(2) Date: Mar. 23, 2022

(87) PCT Pub. No.: WO2021/058236
PCT Pub. Date: Apr. 1, 2021

(65) Prior Publication Data
US 2022/0339404 A1 Oct. 27, 2022

(30) Foreign Application Priority Data

Sep. 25, 2019 (DE) ..................... 10 2019 125 858.8

(51) Int. Cl.
*A61M 25/00* (2006.01)
*A61M 25/10* (2013.01)

(52) U.S. Cl.
CPC ...... *A61M 25/0054* (2013.01); *A61M 25/104* (2013.01); *A61M 2025/0059* (2013.01);
(Continued)

(58) Field of Classification Search
CPC ............ A61M 25/0054; A61M 25/104; A61M 2025/0059; A61M 2025/105;
(Continued)

(56) References Cited

U.S. PATENT DOCUMENTS 4,119,099 A * 10/1978 Patel ..................... A61M 25/10
604/920
4,976,690 A * 12/1990 Solar ................... A61M 25/104
604/103.1
(Continued)

FOREIGN PATENT DOCUMENTS

DE 102013021998 7/2015

OTHER PUBLICATIONS

Internationaler Recherchenbericht und Schriftlicher Bescheid [International Search Report and the Written Opinion] Dated Jan. 14, 2021 From the International Searching Authority Re. Application No. PCT/EP2020/074287 and Its Translation of Search Report Into English. (12 Pages).

*Primary Examiner* — Theodore J Stigell

(57) ABSTRACT

The invention relates to a balloon catheter comprising a shaft (2) extending in the longitudinal direction, which has at least a first and a second section (7, 8), with the first section (7) being arranged distal to the second section (8) and being more flexible than the second section (8), with the shaft (2) being provided with a first and a second hose-like tube (10, 11) and a balloon (3) being arranged at the distal end of the first tube (10), said balloon (3) being expandable by pressurization with a fluid led through said first tube (10), and said second tube (11) serving for accommodating a guidewire and terminating distally of said balloon (3) and being provided with an opening at said distal end, wherein both said first and second tubes (10, 11) extend along said first and second sections (7, 8), and both said first and second tubes (10, 11) are more flexible in said first section (7) than in said second section (8), wherein a transition section (9) is arranged between said first and second sections (7, 8), in which the first tube (10) has the same material properties as in the first section (7) and the second tube (11) has the same material properties as in the second section (8) or (Continued)

Figure 1:
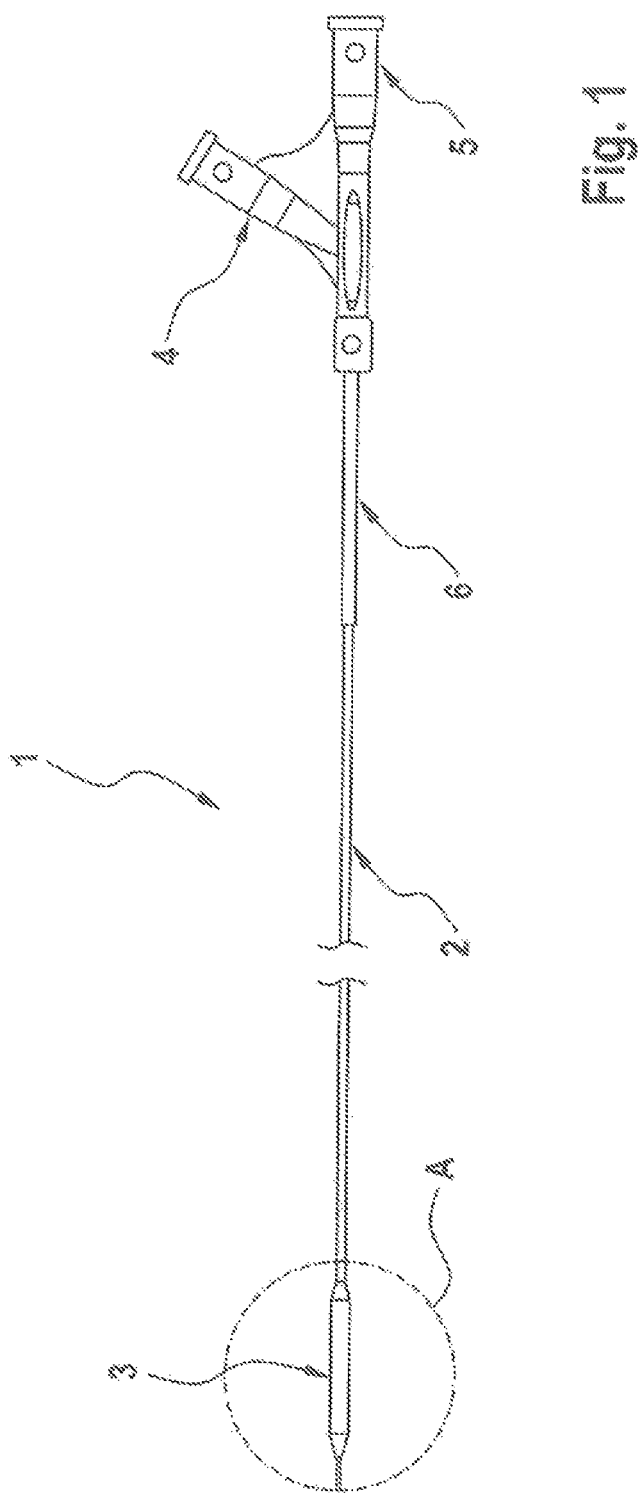

the first tube (10) has the same material properties as in the second section (8) and the second tube (11) has the same material properties as in the first section (7).

17 Claims, 2 Drawing Sheets

(52) U.S. Cl.
CPC ................. *A61M 2025/105* (2013.01); *A61M 2025/1061* (2013.01)

(58) Field of Classification Search
CPC ...... A61M 2025/1061; A61M 25/1006; A61M 2025/1031; A61M 2025/1056; A61M 25/10; A61M 2025/1084; A61F 2250/0067; A61F 2/958; A61B 17/12022; A61B 2017/1205

See application file for complete search history.

(56)     References Cited

U.S. PATENT DOCUMENTS

| | | | | |
|---|---|---|---|---|
| 5,221,260 | A | * | 6/1993 | Burns ................. A61M 25/104 |
| | | | | 604/99.04 |
| 5,304,121 | A | * | 4/1994 | Sahatjian ................ A61L 29/16 |
| | | | | 606/194 |
| 6,702,802 | B1 | * | 3/2004 | Hancock ............... A61M 25/10 |
| | | | | 604/524 |
| 8,088,121 | B2 | | 1/2012 | Nishide et al. |
| 2004/0138731 | A1 | * | 7/2004 | Johnson ................. A61F 2/958 |
| | | | | 623/1.11 |
| 2010/0016937 | A1 | | 1/2010 | Alkhatib |

* cited by examiner

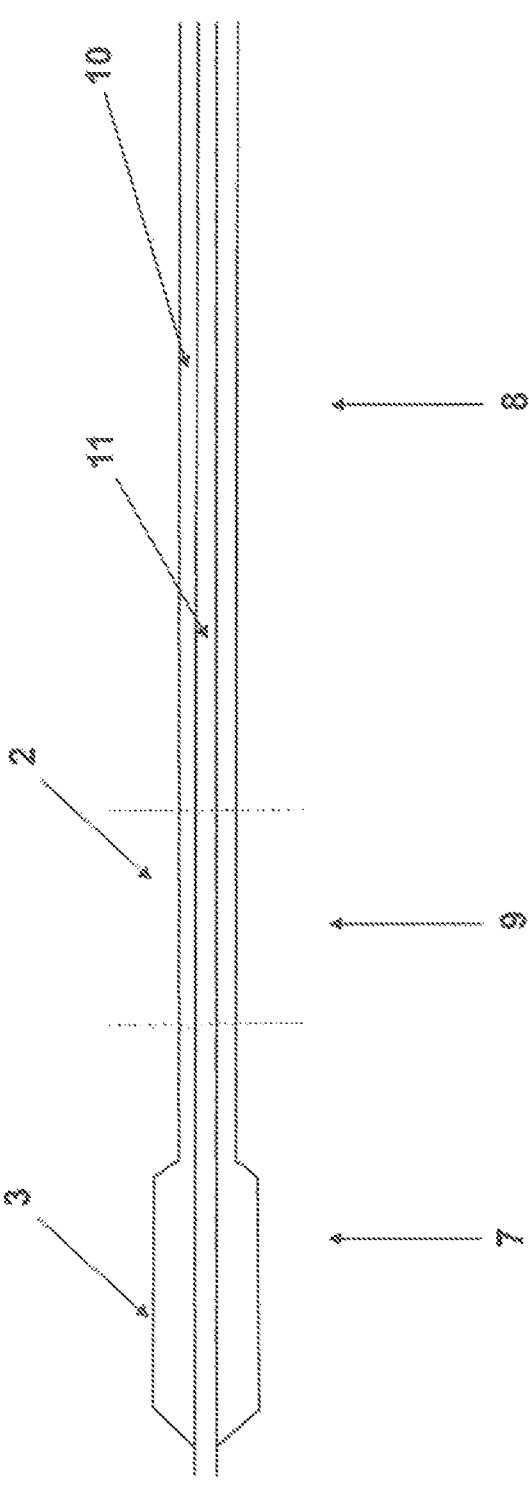

KINK-PROOF BALLOON CATHETER

RELATED APPLICATIONS

This application is a National Phase of PCT Patent Application No. PCT/EP2020/074287 having International filing date of Sep. 1, 2020, which claims the benefit of priority of German Patent Application No. 10 2019 125 858.8 filed on Sep. 25, 2019. The contents of the above applications are all incorporated by reference as if fully set forth herein in their entirety.

FIELD AND BACKGROUND OF THE INVENTION

The invention relates to a balloon catheter having a longitudinally extending shaft comprising at least a first section and a second section, with the first section being located distal to the second section and being more flexible than the second section.

The use of balloon catheters nowadays is standard practice in everyday clinical routine. Their use in the context of intravascular interventions usually involves the widening of constricted vessel areas, either by means of the balloon catheter itself or in combination with other medical devices such as balloon-expandable stents, for example. In case of percutaneous transluminal angioplasty, a balloon catheter is navigated to the site of the stenosis via a guidewire and guide catheter and expanded by means of applying a pressurized fluid (approximately 4 to 12 bar). Deposits present in the area of the stenosis are pressed into the vessel wall. In addition, a stent (vascular endoprosthesis) may be placed in position with a view to keeping the blood vessel permanently open. To prevent a stenosis from recurring due to vasoconstrictive overgrowth of the widened site, drug-eluting balloon catheters can also be put to use, which are designed to dispense a drug such as paclitaxel at the site of vasoconstriction during expansion. When the treatment has been completed and the balloon is subsequently in collapsed state, the balloon catheter is withdrawn from the vascular system and removed.

Frequently chosen as access site for balloon catheters is the femoral artery in the groin. As it runs, at least partially, relatively near the surface, the femoral artery is thus easily accessible for the attending physician, both for treatments to be performed in the coronary area, but also for other areas of the vascular system such as the brain or extremities. Moreover, catheters of relatively large lumen with large outer diameters can be inserted via the femoral artery (inguinal artery).

One problem to be observed when it comes to inserting balloon catheters is the conflict of goals which is, on the one hand, to make the balloon catheter advanceable over relatively long distances, and on the other hand, to have available a sufficiently thin and flexible balloon catheter which is as well capable of being inserted into small narrow-lumen blood vessels. Another important factor to be taken into account is to design the balloon catheter to be as kink-resistant as possible so that the forward movement of the balloon catheter initiated by the attending physician from proximal is transmitted to the distal tip of the balloon catheter without impairing the advancement of the balloon catheter by kinking between the access site and the target position.

In terms of good advanceability and kink resistance, a relatively stiff balloon catheter would be preferable, whereas it would be of advantage to have available utmost flexibility to enable insertion into tortuous blood vessels of narrow lumen. To satisfy these apparently contradictory requirements, balloon catheters are often designed to be relatively stiff in the proximal region and relatively flexible in the distal region. Accordingly, a proximal section may, for example, be made of a metal such as stainless steel, while plastic materials, often a polyamide, may be employed for the more distal sections.

In this context, balloon catheters are also known which are build up using a particularly flexible material in a distal section, a material of medium flexibility in a middle section and a comparatively less flexible material in a proximal section. Basically, this fulfills the criterion of increasing flexibility from proximal to distal, but the transition locations between the individual sections are potentially weak points where kinking of the balloon catheter can occur when it is pushed forward in the distal direction.

SUMMARY OF THE INVENTION

It is thus the objective of the invention to provide a balloon catheter that overcomes this problem and, in particular, has no locations where there is an increased risk of kinking.

As proposed by the invention, this objective is reached by a balloon catheter with a shaft extending in the longitudinal direction, which has at least a first and a second section, with the first section being arranged distal to the second section and being more flexible than the second section, with the shaft being provided with a first and a second hose-like tube and a balloon being arranged at the distal end of the first tube, said balloon being expandable by pressurization with a fluid led through said first tube, and said second tube serving for accommodating a guidewire and terminating distally of said balloon and being provided with an opening at said distal end, wherein both said first and second tubes extend along said first and second sections, and both said first and second tubes are more flexible in said first section than in said second section, wherein a transition section is arranged between said first and second sections, in which

- the first tube has the same material properties as in the first section and the second tube has the same material properties as in the second section or
- the first tube has the same material properties as in the second section and the second tube has the same material properties as in the first section.

The invention is thus based on the idea of creating a transition section between the first and second sections, with the overall flexibility of said transition section being intermediate between that of the first section and that of the second section. This is achieved by the provision that in the transition section the material properties of the first tube differ from those of the second tube. Moreover, material is used, either for the first or for the second tube, which corresponds in terms of properties to that in the first or second section. In other words, the material properties overlap. Although it is true for both the first and second tubes that they are more flexible in the first section than in the second section, the transition between the first, particularly flexible section and the second, less flexible section, however, does not take place at a single position, but ultimately at two positions, namely the distal and proximal ends of the transition section. This will minimize the risk of kinking significantly at the transition from the first to the second section.

In the transition section, the material properties of the first and second tubes are selected such that they overlap. Either the material properties of the first tube in the transition section correspond to those in the first section, while the second tube has the material properties of the second section, or vice versa. This ensures that the material properties of one of the two tubes do not change at the distal and proximal ends of the transition section, i.e. consistent material properties are existing here, which makes the occurrence of kinking considerably less likely. At both the distal and proximal ends of the transition section, only the properties of one of the tubes change, but not the properties of the other tube.

Same as conventional balloon catheters, the balloon catheter proposed by the invention also has at least two tubes, that is, a first tube which serves to supply fluid for the purpose of expanding the balloon, and a second tube which is provided for receiving a guidewire. Accordingly, the balloon is arranged at the distal end of the first tube. When the balloon of the balloon catheter has reached its target site, fluid is introduced into the balloon through the first tube to dilate it and, for example, press deposits existing in the vessels into the vessel wall or alternatively to expand or widen a stent. Subsequently, the fluid is withdrawn through the first tube, whereupon the balloon deflates so that the balloon catheter as a whole can then be pulled out of the vascular system in proximal direction. In this context, the term tube is used to denote a conduit or hose that extends at least partially through the balloon catheter in longitudinal direction and has a lumen extending through the interior of the tube. The tube can have the shape of a hollow cylinder of a circular or elliptical cross-section, but this is not absolutely necessary. As far as the cross-section is concerned, almost any other shape is conceivable. However, a circular or perhaps elliptical cross-section is to be viewed as an advantage since one tube can be easily passed through the other tube, usually running the second tube through the first tube.

The second tube serves the purpose of accommodating the guidewire. Unlike the first tube, this one is not closed distally, but ends distally of the balloon and has an opening at the distal end. The procedure usually adopted is to first advance the guidewire to the target position and then push the balloon catheter forward over the guidewire to the target site, with the guidewire sliding through the second tube.

With regard to the second tube, essentially two different systems are known, namely over-the-wire (OTW) and rapid exchange (Rx) balloon catheters. The balloon catheter according to the invention can be either an OTW or an Rx balloon catheter. While in an OTW catheter the lumen for the guidewire extends from proximal to distal along the entire length of the catheter, an Rx catheter is designed to have a separate guidewire access port (Rx port) where the guidewire exits the catheter significantly distal to the proximal end of the catheter. Accordingly, in the case of an OTW balloon catheter, the tubes, resp. the lumens extending through the tubes for fluid delivery and guidewire run parallel or concentric to each other from the proximal end of the catheter up to the balloon, whereas in the case of an Rx catheter, this is only the case between the Rx port and the balloon. By contrast, the section between the Rx port and the proximal end only has one tube for fluid delivery.

To appropriately adjust the material properties in the first and second sections and in the transition section in the desired way, especially in the first section the first and the second tube may be made of a first material and in the second section the first and the second tube may be made of a second material, with the first material being more flexible than the second material and in the transition section the first tube being made of another material than that of the second tube. For one of the two tubes, the material is thus kept constant between the first section and the transition section, and for the other tube, between the transition section and the second section. In this way, the described overlapping transition between the material properties of the first and second tube is brought about.

Thermoplastic elastomers, for example polyether block amides (PEBA), are the first choice as a particularly flexible or soft material. This is a thermoplastic elastomer obtainable by polycondensation of a carboxylic acid polyamide with a polyether having terminal OH groups. In particular, PEBA is marketed under the tradename of PEBAX® by the Arkema company. In this context, flexible material is understood to mean a material that adapts particularly well to external conditions and is also capable of following fine ramifications of the vascular system, with the terms soft and flexible being used synonymously within the scope of this application.

Alternatively, other polyamides may also be used as first material for the balloon, for example those available from the company of EMS-GRIVORY under the tradename of Grilamid®. Especially preferred is the use of a polyamide 12 (PA 12, Grilamid® L), a polyamide obtainable by the polycondensation of laurolactam. Moreover, further conducively usable polyamides are polyamide 10.10 (PA 10.10, Grilamid® 1S), a polyamide obtained by polycondensation of decandiamine and sebacic acid, polyamide 6.10 (PA 6.10, Grilamid® 2S), a polyamide obtained by polycondensation of hexamethylenediamine and sebacic acid, or polyamide 6.12 (PA 6.12, Grilamid® 2D), a polyamide obtained by polycondensation of hexamethylenediamine and dodecanedioic acid.

A polyamide such as nylon (polyhexamethylene adipic acid amide) can be used, for example, as a second material of medium flexibility. Especially for the first section a material can be used that has a Shore D hardness in the range of between approx. 25 and 72. Appropriate and suitable for the second section are materials having a Shore D hardness ranging between 80 and 85. The exact properties of the polymers can be adjusted by adding additives.

The material from which the balloon itself is made may be the same as or different from the material of the first tube in the first section. For example, the balloon itself may also be made of nylon (polyhexamethylene adipic acid amide), which is a proven material for balloons, even if the first tube in the first section is made of a more flexible material such as a polyether block amide. Other materials that can be used for the balloon are polyurethane, polyolefin copolymers, polyethylene or silicones.

The term balloon as it is used within the scope of the present invention shall be understood to define the element of a balloon catheter that can be expanded by feeding in a fluid, irrespective of the shape or material of said expandable element. Typically, the balloon has an elongated configuration. The fluid may be of gaseous or liquid nature. The fluid can be, for example, water mixed with contrast medium or a saline solution mixed with contrast medium. The nominal pressure for expanding the balloon can be, for example, 4 to 12 bar, preferably 6 to 8 bar. At this pressure, the balloon reaches its nominal diameter in the expanded state. The dimensions of the balloon may vary greatly depending on the field of application; for example, the diameter in the expanded state may range from approx. 1 mm to approx. 50 mm, and the length may range between approx. 5 mm and approx. 300 mm. However, the dimensions may also deviate from this, for example, when using the balloon/balloon catheter for applications in urology or veterinary medicine.

Typically, the deflated balloon of the balloon catheter is laid in folds. As required by the size of the balloon, different numbers of folds may be formed, which are subsequently wound up around the axis of the catheter in the same direction. This arrangement ensures a significant reduction of the diameter.

Alternatively, or in addition to varying the material itself, the material thicknesses of the first and second tubes may also differ in the transition section. Although for the first and second sections, for example, the same materials may be used, their thickness may vary, however. In this case, both the first and the second tubes in the first section are made of a material of comparatively low material thickness, while the first and second tubes in the second section are made of the same (or maybe a different) material the thickness of which is higher, however. In the transition section, however, an overlapping transition is created in such a way that the material properties of one tube match those in the first section and the material properties of the other tube match those in the second section. It thus follows that either the first tube has the same material thickness in the first section and the transition section, while the second tube has the same material thickness in the transition section and the second section, or the first tube has the same material thickness in the transition section and the second section, while the second tube has the same material thickness in the first section and in the transition section. The material thicknesses of the first and second tubes do not necessarily have to coincide in a given section; for example, also the second tube in the first section may have a material thickness that is lower than that of the first tube. However, it is in fact important to note that for the first and second tubes the transition of material thicknesses does not occur at a single point along the longitudinal axis of the balloon catheter, but is offset from each other in the manner described herein.

When creating a transition section by varying the material thicknesses, nylon (polyhexamethylene adipic acid amide), for example, may be employed as the material for the first and second tubes, with the deviating properties being brought about by selecting a higher or lower material thickness, instead of by varying the material itself.

Within the context of the invention, proximal is understood to mean in the direction of the exterior of the body, i.e., toward the attending physician, while distal shall be understood to denote the opposite direction, that is, toward the blood vessel being treated. Radial refers to the plane perpendicular to the longitudinal axis of the balloon catheter.

The first and second tubes may extend parallel to each other in the areas where both tubes are arranged; it is preferred for the second tube, however, to extend at least partially through the first tube. Accordingly, there is a concentric configuration of the first and second tube. In this case, the second tube is normally on the inside, which means that the guidewire is passed through the inner second tube of the balloon catheter, with the first tube radially surrounding the second tube.

Proximal to the second section another proximal section is provided. Typically, this proximal section has less flexibility than the first or second section, but nevertheless constitutes a major portion of the overall length of the balloon catheter. It is also possible to provide further sections between the second section and the proximal section. As regards the proximal section, it is to be noted that the focus is less on flexibility and more on advanceability and kink resistance. Therefore, the proximal section may be made of a metal, in particular of stainless steel, for example. However, it is equally conceivable to provide a proximal section made of a polymer, with said polymer being typically stiffer than the polymers employed for the first and second sections as well as the transition section.

At the proximal end of the balloon catheter, adjacent to the shaft, a so-called catheter hub is usually provided, which is a connector for the device used to deliver fluid and effect pressurization. The connector, for example, can be a conventional luer or luer-lock connection. It is particularly expedient to provide two Luer lock connectors, typically female connectors, one for connecting the first lumen to a balloon dilator and another for inserting the guidewire into the balloon catheter. The connectors may, for example, consist of a polycarbonate. At its proximal end the guidewire extending through the balloon catheter may be held by means of a torquer which facilitates handling the usually very thin guidewire.

To make sure the transition section fulfills the intended role as a safeguard against any undesirable kinking of the balloon catheter, said section should have a length of $\geq 3$ cm, preferably range between 3 and 10 cm. A length of the transition section of 5 to 7 cm is particularly preferred. A transition section that is too short in length may fail to bring about the desired kink protection, whereas too long a transition section may not be suitable for insertion into narrow-lumened blood vessels.

A length of the first section ranging between 3 and 20 cm, in particular 5 to 15 cm, and a length of the second section of between 5 and 35 cm, in particular 20 to 30 cm have proven advantageous. In this respect, the length of the first section is understood to be the length from the distal tip of the balloon catheter to the beginning of the transition section. More often than not, the total length of the balloon catheter exceeds 1 m, so that insertion in the groin region is possible, with the balloon catheter capable of being advanced to a wide variety of sites in the vascular system. The proximal section alone often has a length $\geq 1$ m.

A typical outside diameter of the first tube in the first section amounts 0.8 to 1.0 mm, in particular is approx. 0.9 mm. The inside diameter typically ranges between 0.7 and 0.8 mm. The outside diameter of the second tube may for example amount to 0.5 or 0.6 mm, the inside diameter of the second tube may range between 0.4 and 0.5 mm. This is especially the case if the second tube extends through the first tube. In the second section, the outer diameter of the first tube may be slightly higher than in the first section and may, for example, range between 0.9 and 1.1 mm. The inside diameter of the first tube in the second section in most cases ranges between 0.8 and 0.9 mm, whereas the dimensions of the second tube largely coincide with those in the first section.

Balloons provided with a coating of active substances can be employed to prevent re-narrowing in the treated section of the vessel following an otherwise successful angioplasty. Restenosis is usually due to cell proliferation in the respective vessel segment resulting in cells of the blood vessel growing into the vessel lumen and are thus causing an obstruction of the blood flow. To prevent this, balloon catheters coated with drugs that inhibit proliferation are increasingly being used. Appropriate drugs usually act in particular on the smooth muscle cells (SMC) and are thus intended to prevent restenosis caused by excessive growth of these cells. The medication is applied to the outside of the balloon and is transferred during balloon dilatation from the balloon to or into the inner vessel wall.

The active substance used is, in particular, a drug or medical substance, preferably a medicinal product that has an inhibitory effect on proliferation and prevents a vasocon-strictive overgrowth of the site dilated by the balloon. Similarly, it may be a hormone-like or regulatory agent capable of influencing organ-specific effects or regulatory functions on certain cells. The active substance or agent may in particular be selected from the following: Tretinoin, orphan receptor agonists, elafin derivatives, corticosteroids, steroid hormones, paclitaxel, rapamycin, tacrolimus, hydro-phobic proteins as well as substances modifying cell prolif-eration. Mixtures of these active substances may also be used. Moreover, derivatives of the above cited active agents may also be of use, wherein said derivatives may in par-ticular be salts, esters, and amides. As steroid hormones methylprednisolone, dexamethasone or estradiol may be used, for example. Particularly preferred is the use of paclitaxel, rapamycin or tacrolimus or relevant derivatives.

Generally speaking, however, the term active substance or agent is to be understood broadly, i.e. it can basically refer to any coatings on the balloon of the balloon catheter that are intended to achieve a specific effect at the target site. When introduced into blood vessels, this effect may in particular be focused on inhibiting cell proliferation. In other medical fields, however, the desired effect may be different, for example in the field of urology involving bladder catheters, where the coating is intended to serve in particular to inhibit bacterial colonization. Heparin, for example, can be used as active agent here.

Coating the surface of the balloon with the active sub-stance is typically achieved by bringing the surface of the balloon in contact with a solution of the active substance, which can be done in particular by immersing the balloon in the solution. Usually, the immersion does not take more than 1 minute, typically ranges between 10 and 30 s. After immersion, the balloon should be drawn out of the first solution at a rate of up to 10 mm/s. It is even more favorable if extraction takes place at a speed of less than 5 mm/s, preferably at a speed ranging between 0.5 mm/s and 2 mm/s. Withdrawing the balloon slowly enables the surface to dry gradually and slowly.

Before coating the balloon, it is useful to clean the surface of the balloon. This can be done, for example, using an appropriate solvent, such as the solvent which is also used for the application of the active agent.

The solution may be saturated with respect to the active agent, but this is not a mandatory requirement. Solvents that can be employed are, for example, methylene chloride, chloroform, alcohol, in particular ethanol, methanol or iso-propanol, acetone, diethyl ether, liquid hydrocarbons, such as, for example, pentane, hexane, heptane, cyclohexane or octane, toluol, tetrahydrofuran (THF) or ethyl acetate. Fur-thermore, solvent mixtures or blends may also be employed. Preferably, the active substance is dissolved in methylene chloride.

As an alternative to coating the balloon by immersion, other methods may also be adopted, for example spraying.

The balloon catheters proposed by the invention can be used in blood vessels, particularly in the field of angioplasty. In this case, the target site of the balloon is a blood vessel, with blood vessels in different areas may be treated, par-ticularly in coronary, intracranial, and peripheral areas. However, balloon catheters may also be employed for other medical applications. A field of application includes urology, where balloon catheters are inserted into the urinary bladder as bladder catheters. The catheter is secured to the balloon. The balloon in this case may be provided for instance with a coating that prevents bacterial colonization and incrusta-tion, for example using heparin.

In pulmonology, balloon catheters can be used to dilatate or occlude a bronchus. Balloon catheters can also be employed in the field of gynecology. In the field of ortho-pedics, balloon catheters can be put to use for the treatment of vertebral fractures with a view to realigning the vertebrae by means of balloon expansion techniques (balloon kypho-plasty). In principle, the balloon catheter proposed by the invention can be used in all fields of medicine in which balloon catheters are employed, with the balloon catheter having special significance when an insertion into blood vessels of narrow lumen is needed.

Furthermore, the inventive balloon catheter may not only serve for the elimination of stenoses and local administration of active substances but additionally for the placement of a stent (endoprosthesis) in a body lumen. Stents are tubular supporting structures implanted into a body lumen, for example a blood vessel, with a view to keeping it perma-nently open. Stents of this nature may be of self-expanding design or expanded with the help of a balloon. For this purpose, the stent is crimped onto the balloon and introduced into the body lumen with the aid of a balloon catheter. At the desired placement site, the balloon is inflated by feeding in a fluid, which also causes the stent to expand and thus be anchored in the body lumen. Moreover, using the inventive balloon enables the relevant active substance to be applied to the wall of the body lumen. Finally, the balloon is deflated and removed from the body lumen whereas the stent remains in place in the lumen.

Over the length of the balloon catheter radiopaque mark-ers may be arranged at various positions, said markers serving the purpose of making the catheter visible on radiographs. In particular, said markers may be manufac-tured of platinum or a platinum alloy such as platinum-iridium.

BRIEF DESCRIPTION OF THE SEVERAL VIEW OF THE DRAWINGS

Further elucidation of the invention is provided through the enclosed figures by way of examples, where FIG. 1 is a side view of the balloon catheter according to the invention;

FIG. 2 is a longitudinal section of the distal portion of the shaft of the balloon catheter shown in FIG. 1.

DESCRIPTION OF SPECIFIC EMBODIMENTS OF THE INVENTION

In FIG. 1, the balloon catheter 1 proposed by the invention is shown in side view, where in the representation chosen here right means proximal and left means distal. The balloon catheter 1 comprises a shaft 2 extending in longitudinal direction, the outer diameter of said shaft being larger in the proximal section 6, of which only a short segment is shown here, than further distally. The section of the shaft 2 in which the balloon 3 is located is identified by the letter A. A first lumen for the fluid delivery as well as a second lumen for accommodation of the guidewire extend through the shaft 2 (not shown here), with the two lumens each being formed by a tube.

Proximally, two catheter hubs in the form of luer-lock connections 4, 5 are arranged at the proximal section 6 of the shaft 2, with connection 4 serving to deliver fluid into the first lumen by means of a balloon dilator and connection 5 serving to introduce the guidewire into the second lumen.

In FIG. 2, only the distal part of the shaft 2 is shown. A first tube 10 is designed so as to accommodate the second tube 11, that is, the second tube 11 extends longitudinally through the first tube 10. At its distal end, the first tube 10 is connected to the balloon 3, which can be expanded by feeding in fluid through the first tube 10, whereas the second tube 11, on the other hand, has been provided with an opening at the distal end and is used to accommodate the guidewire, which is not shown here.

The portion of the shaft 2 shown here (excluding the proximal section 6 of FIG. 1) has a first section 7 and a second section 8, with the first section 7 being located distal to the second section 8. However, first and second sections 7, 8 are not directly adjacent to each other; instead, a transition section 9 is arranged between the first section 7 and the second section 8. In the transition section 9, the first tube 10 in the example selected here is made of the same material as in the first section 7, for example made of PEBAX®. On the other hand, the second tube 11 is made of the same material in the transition section 9 as in the second section 8, for example made of nylon. The transition from the stiffer to the more flexible material thus occurs at different points for the first and second tubes 10, 11, in one case at the transition from the second section 8 to the transition section 9, in the other case at the transition from the transition section 9 to the first section 7. The properties of the other tube, however, remain unchanged at the relevant places, resulting in the risk of kinking being significantly reduced. In the present example, the first tube 10 (including balloon area) has a length of 15 cm at the distal end for the softer material and further proximally a length of 25 cm for the less soft material. On the other hand, the second tube 11 has a length of 10 cm at the distal end for the softer material and further proximally a length of 30 cm for the less soft material. Thus, the first section 7 has a length of 10 cm, the transition section 9 of 5 cm and the second section 8 of 25 cm.

What is claimed is:

1. A balloon catheter comprising a shaft extending in the longitudinal direction, the shaft having at least a first and a second section, with the first section being arranged distal to the second section and being more flexible than the second section, with the shaft being provided with a first and a second hose-like tube and a balloon being arranged at a distal end of the first tube, said balloon being expandable by pressurization with a fluid led through said first tube, and said second tube serving for accommodating a guidewire and terminating distally of said balloon and being provided with an opening at a distal end of the second tube, wherein both said first and second tubes extend along said first and second sections, and both said first and second tubes are more flexible in said first section than in said second section, wherein a transition section is arranged between said first and second sections, in which a transition takes place at a distal and a proximal end of the transition section, wherein said transition section is a single transition section of pre-determined length, wherein at both the distal and proximal ends of the transition section, only the properties of one of the tubes change, but not the properties of the other tube, wherein only one of the following applies:

(i) within the transition section the first tube has the same material properties as in the first section and the second tube has the same material properties as in the second section and (ii) within the transition section the first tube has the same material properties as in the second section and the second tube has the same material properties as in the first section.

2. The balloon catheter according to claim 1, wherein in the first section the first and the second tube are made of a first material and in the second section the first and the second tube are made of a second material, with the first material being more flexible than the second material and in the transition section the first tube being made of another material than that of the second tube.

3. The balloon catheter according to claim 2, wherein the first material is a thermoplastic elastomer.

4. The balloon catheter according to claim 2, wherein the second material is a polyamide.

5. The balloon catheter according to claim 1, wherein the material thicknesses of the first and second tubes differ in the transition section.

6. The balloon catheter according to any one of claims 1 to 5, characterized in that the second tube extends at least partially through the first tube.

7. The balloon catheter according to claim 1, wherein a proximal section is arranged proximal to the second section.

8. The balloon catheter according to claim 7, wherein the shaft in the proximal section is at least partially made of metal.

9. The balloon catheter according to claim 8, wherein the shaft in the proximal section is at least partially made of stainless steel.

10. The balloon catheter according to claim 1, wherein the transition section has a length of ≥3 cm.

11. The balloon catheter according to claim 10, wherein the transition section has a length ranging between 3 and 10 cm.

12. The balloon catheter according to claim 1, wherein the length of the first section ranges between 3 to 20 cm.

13. The balloon catheter according to claim 12, wherein the length of the first section ranges between 5 and 15 cm.

14. The balloon catheter according to claim 1, wherein the length of the second section ranges between 5 to 35 cm.

15. The balloon catheter according to claim 14, wherein the length of the second section ranges between 20 and 30 cm.

16. The balloon catheter according to claim 1, wherein the balloon is coated with one or more active substances.

17. The balloon catheter according to claim 16, wherein the active substance used is selected from the following group: Tretinoin, orphan receptor agonists, elafin derivatives, corticosteroids, steroid hormones, paclitaxel, rapamycin, tacrolimus, hydrophobic proteins, heparin and/or hormone-like or cell proliferation-modifying substances.

* * * * *